United States Patent
Wu

(10) Patent No.: US 11,104,948 B2
(45) Date of Patent: Aug. 31, 2021

(54) NGS SYSTEMS CONTROL AND METHODS INVOLVING THE SAME

(71) Applicant: VELA OPERATIONS SINGAPORE PTE. LTD., Singapore (SG)

(72) Inventor: Mengchu Wu, Singapore (SG)

(73) Assignee: VELA OPERATIONS SINGAPORE PTE. LTD., Singapore (SG)

(*) Notice: Subject to any disclaimer, the term of this patent is extended or adjusted under 35 U.S.C. 154(b) by 206 days.

(21) Appl. No.: 15/117,656

(22) PCT Filed: Feb. 10, 2015

(86) PCT No.: PCT/IB2015/050990
§ 371 (c)(1),
(2) Date: Aug. 9, 2016

(87) PCT Pub. No.: WO2015/118513
PCT Pub. Date: Aug. 13, 2015

(65) Prior Publication Data
US 2018/0037949 A1 Feb. 8, 2018

(30) Foreign Application Priority Data
Feb. 10, 2014 (GB) .................... 1402249

(51) Int. Cl.
| C12Q 1/68 | (2018.01) |
|---|---|
| C12Q 1/6874 | (2018.01) |
| C12Q 1/6886 | (2018.01) |
| C12Q 1/6888 | (2018.01) |

(52) U.S. Cl.
CPC ......... *C12Q 1/6874* (2013.01); *C12Q 1/6886* (2013.01); *C12Q 1/6888* (2013.01); *C12Q 2600/166* (2013.01)

(58) Field of Classification Search
CPC ................................................ C12Q 2600/166
See application file for complete search history.

(56) References Cited

U.S. PATENT DOCUMENTS

| 5,596,132 A | 1/1997 | Zaitlin et al. | |
|---|---|---|---|
| 2007/0015139 A1* | 1/2007 | Gayral | C12N 1/06 435/5 |
| 2011/0207624 A1 | 8/2011 | Shen et al. | |
| 2013/0296176 A1* | 11/2013 | Marziali | C12Q 1/6816 506/6 |
| 2015/0087535 A1* | 3/2015 | Patel | C12Q 1/6858 506/4 |

FOREIGN PATENT DOCUMENTS

| WO | 95/21248 A1 | 8/1995 |
|---|---|---|
| WO | 87/06261 A1 | 1/1997 |
| WO | 00/50632 A3 | 8/2000 |
| WO | 01/72996 A1 | 10/2001 |
| WO | 2012/125848 A2 | 9/2012 |
| WO | 2013/175365 A1 | 11/2013 |
| WO | 2014/082032 A1 | 5/2015 |

OTHER PUBLICATIONS

Meyer M, Kircher M. Illumina sequencing library preparation for highly multiplexed target capture and sequencing. Cold Spring Harb Protoc. Jun. 2010; 2010 (6):pp. 1-20. (Year: 2010).*
Cottrell et al. Validation of a next-generation sequencing assay for clinical molecular oncology. J Mol Diagn. Jan. 2014; 16(1):89-105. Epub Nov. 6, 2013. (Year: 2014).*
Dreier J, Störmer M, Kleesiek K. Use of bacteriophage MS2 as an internal control in viral reverse transcription-PCR assays. J Clin Microbiol. Sep. 2005; 43(9):4551-7. (Year: 2005).*
Iker et al. Evaluation of commercial kits for the extraction and purification of viral nucleic acids from environmental and fecal samples. J Virol Methods. Jul. 2013; 191(1):24-3.0 Epub Apr. 8, 2013. (Year: 2013).*
Jiang L, Schlesinger F, Davis CA, Zhang Y, Li R, Salit M, Gingeras TR, Oliver B. Synthetic spike-in standards for RNA-seq experiments. Genome Res. Sep. 2011; 21(9):1543-51. Epub Aug. 4, 2011. (Year: 2011).*
Sachsenröder J, Twardziok S, Hammerl JA, Janczyk P, Wrede P, Hertwig S, Johne R. Simultaneous identification of DNA and RNA viruses present in pig faeces using process-controlled deep sequencing. PLoS One. 2012; 7(4):e34631. pp 1-11. (Year: 2012).*
Buehler B, Hogrefe HH, Scott G, Ravi H, Pabón-Peña C, O'Brien S, Formosa R, Happe S. Rapid quantification of DNA libraries for next-generation sequencing. Methods. Apr. 2010; 50(4):S15-8. (Year: 2010).*
Kleiboeker SB. Applications of competitor RNA in diagnostic reverse transcription-PCR. J Clin Microbiol. May 2003; 41(5):2055-61. (Year: 2003).*
Taly et al. Multiplex picodroplet digital PCR to detect KRAS mutations in circulating DNA from the plasma of colorectal cancer patients. Clin Chem. Dec. 2013; 59(12): 1722-31. Epub Aug. 12, 2013. (Year: 2013).*
Taly et al. (2013, Supporting document, pp. 1-19) Clin Chem. Dec. 2013; 59(12):1722-31. Epub Aug. 12, 2013. (Year: 2013).*
Bullard et al., Evaluation of Statistical Methods for Normalization and Differential Expression in mRNA-Seq Ezperiments, BMC Bioinformatics 2010, 11:94, http://www.biomedcentral.com/1471-2105/11/94, pp. 1-13.
Singapore Application No. 11201604202Q—ISR and Written Opinion—dated Oct. 31, 2017.
Genome Research, 2011, and vol. 21, No. 9 and pp. 1543-1551.
Japanese Patent Office Action for JP 2016-544852, dated Aug. 8, 2018.
L. Jiang et al: "Synthetic spike-in standards for RNA-seq experiments", Genome Research, vol. 21, No. 9, Aug. 4, 2011 (Aug. 4, 2011), pp. 1543-1551, XP055152443, ISSN: 1088-9051, DOI: 10.1101/gr.121095.111. the whole document.

(Continued)

*Primary Examiner* — Teresa E Strzelecka
*Assistant Examiner* — Olayinka A Oyeyemi
(74) *Attorney, Agent, or Firm* — Hahn Loeser & Parks LLP; John J. Cunniff

(57) ABSTRACT

The present invention relates to controls for NGS methods. The present application discloses plasmids, kits, their uses and methods involving the controls according to the present invention.

14 Claims, 6 Drawing Sheets

(56) References Cited

OTHER PUBLICATIONS

Figure 1:
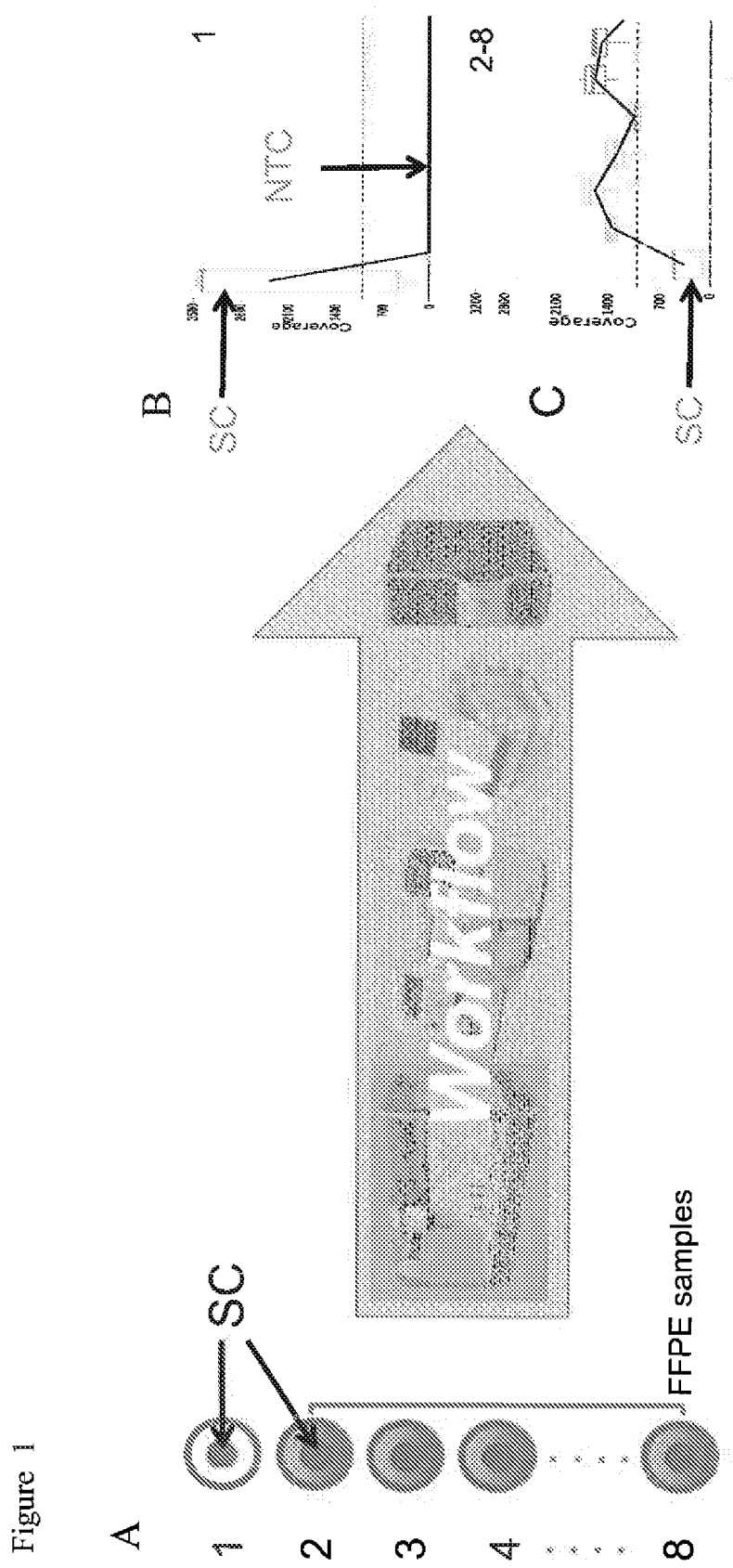

Quail Michael A. et al: "SASI-Seq: sample assurance Spike-Ins, and highly differentating 384 barcoding for Illumina sequencing", BMC Genomics, vol. 15, Feb. 7, 2014 (204-02-07), XP002738563. the whole document.
Kovalic David et al.: "The Use of Next Generation Sequencing and Junction Sequence Analysis Bioinformatics to Achieve Molecular Characterization of Crops Improved Through Modern Biotechnology", Plant Genome, vol. 5, No. 3, Nov. 2012 (Nov. 2012), pp. 149-163, XP002738564, ISSN: 1940-3372 (print) the whole document.
Using a PhiX control for HiSeq sequencing runs, 2013, Available from: http://support.illumina.com/content/dam/illumina-marketing/documents/products/technotes/technote_phixcontrolv3.pdf. [accessed Oct. 20, 2014].
Int. J. Cancer, vol. 131, 2012, ganzenmueller, T. et al., "Next-generation sequecing fails to identify . . . ", pp. E1173-E1179. Available online: http://onlinelibrary.wiley.com/doi/10.1002/ijc.27581/pdf.
BMC Genomics, vol. 12, 2011, Meil Lingking, et al., "AluScan; a method for genome-wide scanning . . . ", Article No. 564. Available at: http://www.biomedcentral.com/content/pdf/1471-2164-12-564.pdf.

* cited by examiner

Figure 6 – Table 1

| Spike-in SC | Spike-in ST | Sample | Conclusion |
|---|---|---|---|
| +/- | + | + | Successful run |
| +/- | + | - (some amplicons) | Deletions in tumor DNA, PCR inhibition in sample. Variant calling in successful amlicons is possible. |
| + | + | - (all amplicons) | Low quality sample (DNA < LOD) |
| - | + | - (all amplicons) | Strong PCR inhibition in sample |
| - | - | - | General workflow failure |
| +/- | - (no TMV amplicon) | + | Possible workflow failure, results are not reliable |
| +/- | - (variant call errors) | + | Possible false positive / false negative variant calls |
| +/- | - (human amplicons) | + | Possible contamination |

NGS SYSTEMS CONTROL AND METHODS INVOLVING THE SAME

CROSS-REFERENCE TO RELATED APPLICATIONS

The present application is a U.S. National Stage entry under 35 U.S.C. § 371 of International Application No. PCT/IB2015/050990 filed on Feb. 10, 2015, designating the United States of America and published in English on Aug. 13, 2015, which in turn claims priority to Great Britain Application No. 1402249.5, filed on Feb. 10, 2014, each of which is hereby incorporated by reference in its entirety.

FIELD OF THE INVENTION

The present invention relates to controls for next generation sequencing assays. These controls can serve as a positive and negative controls and as extraction control, respectively. The present application describes corresponding plasmids, kits, their uses and a method involving the use of controls of the present invention.

BACKGROUND OF THE INVENTION

The use of nucleic acid sequencing has become an essential tool in many diagnostic areas in modern medicine. In particular, Next Generation Sequencing (NGS)-based genetic tests are quickly gaining acceptance in clinical diagnostics. An example of such an area is oncology, where nucleic acid sequencing is employed in order to identify whether e.g. oncogenic mutations are present in a gene or whether cancer-inducing and/or indicating translocations are present in a genome. Further, nucleic acid sequencing is employed to detect whether a pathogenic microorganism (such as e.g. a bacteria or a virus) is present in a clinical sample, e.g. a tissue sample or a blood sample from a human patient. In the latter method, nucleic acid sequences are detected, which are not found in a human subject but only in the microorganism.

Typically, the actual sequencing step is preceded by an amplification reaction in order to amplify the nucleic acid to be sequenced. Such an amplification reaction is usually carried out by a PCR reaction; thus, specific primers are used in the PCR reaction, which hybridize to sequences upstream and downstream of the sequence to be amplified (i.e. the primers flank the sequence to be amplified).

Due to progress in the recent years, many steps during diagnostic methods, including NGS workflow, have been automated. For example, the extraction of nucleic acids from a clinical sample, the amplification reaction as well as the actual sequencing reaction are carried out automatically.

NGS methods may result in the identification and sequence determination of a target sequence, which may indicate the presence or absence of an oncogenic mutation or the presence or absence of a pathogen-derived nucleic acid.

It can, however, not be excluded in an assay as described above that certain steps of the assay have been conducted improperly. Whereas, conventional assays relying on PCR (e.g. qPCR) typically involve the use of positive and negative controls to assure the quality of the results, NGS-based assays generally do not contain such controls. This may cause problems in the correct interpretation of the sequencing results.

A typical example of an improperly conducted assay is that a target sequence is not detected because the extraction step has not been carried out properly. Thus, an oncogene or an infectious microorganism might indeed be present in the sample although the result, i.e. the outcome of the sequencing reaction will be that the sequencing reaction has failed, or the analysis subsequent to the sequencing reaction will classify such event as "invalid" result. When the sample is contaminated with DNA, the outcome of analysis of the sequencing reaction will be that the result is false positive or false negative. result). Controls provided herein, which include a negative control permit users of high-throughput sequencing methods (also referred to as Next Generation Sequencing) to recognize potential false positive and false negative results. The system controls (SC) provided herein will assist in troubleshooting sequencing failure. Although sequencing failure does not put a risk on patients, it is still important due to the high costs involved in NGS processes. Further, the analysis of sequencing data obtained in NGS including appropriate systems controls as provided herein is more reliable, faster and more accurate.

In order to exclude an improper extraction step, extraction controls can be used. Extraction control may comprise addition of intact so-called reference cells comprising a control nucleic acid sequence, that usually differs from the sequence to be detected. Such cells are typically added ("spiked") to the sample prior to the automated extraction step (usually via adding the cells in a specific concentration to the lysis buffer used during the extraction). The detection of a sequence of the extraction control after completion of the assay indicates that the extraction step has indeed been carried out properly.

It has also to be ensured that the amplification and actual sequencing steps function under the conditions applied and that the limit of detection of target nucleic acids is sufficient to make a clear statement with respect to the quality and quantity of the result, i.e. to state that a specific sequence is present or absent in a sample with a certain level of accuracy.

Further, it has to be carefully ruled out that contaminating nucleic acids lead to false positive or false negative results. As mentioned above, the presence of contaminating nucleic acids may in the analysis of the NGS data give the impression that a certain target sequence (or nucleic acid sequence of interest) is present in a sample from a patient. On the other hand, when the NGS sequencing reaction aims at determining the presence or absence of a wild-type target sequence and of a variant sequence (e.g. in an oncogene), the contamination may cause the overall sequencing results to shift to a side where either the wild-type or the variant is over- or underrepresented. This may also change the overall outcome of the NGS-based diagnosis, e.g. when a pre-determined level of expectancy is fixed.

Summarizing the above, the controls disclosed herein, which may also be designated as "Systems Control" (SC) are required for diagnostic testing involving NGS, particularly when assays have to meet certain regulatory requirements of respective regulatory authorities, such as the FDA. At the same time, these controls should be readily available, i.e. obtainable without using complex molecular biological techniques, they should be producible at low cost, without constituting a hazard to the environment or staff handing them. Further, the presence of controls should not adversely affect the sensitivity of the diagnostic assays. These and other objectives are fulfilled by the present invention.

The inventors of the present invention inter alia succeeded in providing system controls for Next Generation Sequencing (NGS) reactions which may be used as positive and negative as well as extraction controls in a NGS reaction.

Before some of the embodiments of the present invention are described in more detail, the following definitions are introduced.

Definitions

As used in the specification and the claims, the singular forms of "a" and "an" also include the corresponding plurals unless the context clearly dictates otherwise.

It needs to be understood that the term "comprising" is not limiting. For the purposes of the present invention, the term "consisting of" is considered to be a preferred embodiment of the term "comprising". If hereinafter a group is defined to comprise at least a certain number of embodiments, this is also meant to encompass a group which preferably consists of these embodiments only. When a nucleic acid control or a target nucleic acid sequence comprises a nucleic acid (sequence) that means that the presence of additional residues in the sequence comprising the other is possible, e.g in plasmid comprising control nucleic acid sequences.

The expressions "target nucleic acid sequence-specific NGS-based diagnostic method" or "NGS-based target nucleic acid detection method" indicate that these methods comprise Next Generation Sequencing, but that additional steps are possible, e.g. extraction and/or purification of nucleic acids from a given sample, any modification of the NGS-protocol as long as the sequencing reaction is conducted according to methods known in the field, and also post-sequencing steps, e.g. analysis, presentation of the data obtained during sequencing and analysis or presentation of results provided at the end of the analysis.

When a control sequence and a target nucleic acid sequence are different, this means that the nucleic acid differ at least in one nucleic acid residue. Frequently, these sequences are from different genes, very frequently they are derived from different genes and organisms. It is preferred that the control nucleic acids are derived from sources or have been modified in such way that said controls do not present any risk for the environment, in particular for the staff in the laboratory dealing with them.

The term "detecting the presence" as used herein is to be understood in the meaning of "detecting the presence or absence".

As mentioned in the method as claimed in the present application, a sample to be analyzed in an high-throughput sequencing or Next Generation Sequencing, i.e. NGS-based diagnostic method potentially comprises a nucleic acid comprising a target sequence. Preferably, the high-throughput sequencing method is a ion semiconductor sequencing method.

In the context of the present invention the term "nucleic acid" refers to a naturally occurring deoxyribonucleotide or ribonucleotide polymer in either single-or double-stranded form. The nucleic acid may particularly be double-stranded DNA and singled-stranded RNA.

The term "sequence" as used herein refers to the sequential occurrence of the bases in a deoxyribonucleotide or ribonucleotide polymer, wherein a base found in a deoxyribonucleotide polymer is selected from the group consisting of A, T, G and C and a base found in a ribonucleotide polymer is selected from the group consisting of A, U, G and C. A sequence of bases in a deoxyribonucleotide polymer may thus e.g. be GGAAGCAAGCCT, whereas a sequence of bases in a ribonucleotide polymer may e.g. be GGAAUCGAU.

As used herein, the term "sample" refers to any biological sample from any human or veterinary subject that may be tested for the presence of a nucleic acid comprising a target sequence. The samples may include tissues obtained from any organ, such as for example, lung tissue; and fluids obtained from any organ such as for example, blood, plasma, serum, lymphatic fluid, synovial fluid, cerebrospinal fluid, amniotic fluid, amniotic cord blood, tears, saliva, and nasopharyngeal washes. As listed above, samples may also be derived from a specific region in the body, e.g. the respiratory tract; samples from the respiratory tract include throat swabs, throat washings, nasal swabs, and specimens from the lower respiratory tract.

The sample may be derived from a human or a veterinary subject. Accordingly, a "patient" may be a human or veterinary subject. If reference is made to a "clinical sample", this indicates that the sample is from a patient suspicious of carrying a nucleic acid comprising a target sequence.

A control sample according to the present invention is prepared by addition of control nucleic acids to a sample, e.g. when the sample is FFPE material from a human organ, the control sample comprises FFPE material from the same source, but in addition it comprises a control nucleic acid that was added to the sample. The control nucleic acid may be added to the control sample prior or after extraction, depending on the step that should be controlled, e.g. extraction, and/or sequencing, etc.

As used herein, the term "amplification" refers to enzyme-mediated procedures that are capable of producing billions of copies of nucleic acid target. Examples of enzyme-mediated target amplification procedures known in the art include PCR.

"Extracting nucleic acids" means that any nucleic acids present in a vial are isolated from any cellular background, particularly isolated from intact cells or tissues. Preferably, the nucleic acids are also washed during the process and optionally concentrated. Following extraction, all cellular or tissue debris not related to nucleic acids has been removed. Typical extraction methods may include the use of hypotonic lysis buffer, heat and/or detergents, and are known to the skilled person.

The term "sequencing" is used herein in its common meaning in molecular biology. Thus, the exact sequential occurrence of bases in a nucleic acid sequence is determined.

The term "microorganism" as used herein is used in its broadest meaning. Thus, a microorganism may be any type of bacteria, archaeum, protozoum, fungus and virus. It is explicitly mentioned that viruses fall under the definition of a "microorganism" as used herein.

The term "oncogene" is used herein in its common meaning in molecular biology and oncology, respectively. Thus, there are e.g. mutations known in genes, which render a "normal or wild-type" gene oncogenic, i.e. cancer-inducing; examples in this respect are mutations rendering kinases constitutionally active such that specific signals (e.g. growth inducing signals) are constantly signaled and corresponding processes initiated. "Oncogenes" as used herein may also relate to intra- or inter-chromosomal translocations resulting also in cancer-inducing situations.

A "target sequence" as referred to herein is a sequence in the nucleic acid, the presence of which is detected in the methods according to the present invention; a "target sequence" is characteristic for the specific nucleic acid, the presence of which is detected.

As used herein, the nucleic acid being sequenced is referred to as the target nucleic acid (or "target"). Target nucleic acids include but are not limited to DNA such as but not limited to genomic DNA, mitochondrial DNA, cDNA and the like, and RNA such as but not limited to mRNA, miRNA, and the like. The target nucleic acid may derive from any source including naturally occurring sources or synthetic sources. The nucleic acids may be PCR products, cosmids, plasmids, naturally occurring or synthetic library members or species, and the like. The invention is not intended to be limited in this regard. The nucleic acid may be from animal or pathogen sources including without limitation mammals such as humans, and microbes such as bacteria, viruses, fungi, parasites, and mycobacteria. In some embodiments, the nucleic acid is not a viral nucleic acid. The target nucleic acid can be obtained from any bodily fluid or tissue including but not limited to blood, saliva, cerebrospinal fluid ("CSF"), skin, hair, urine, stool, and mucus. The target nucleic acid may also be derived from without limitation an environmental sample (such as a water sample), a food sample, or a forensic sample, the sample may be a fresh sample (e.g. biopsy material directly subjected to nucleic acid extraction), or a sample that has been treated to allow storage, e.g. a sample that was formalin-fixed and/or paraffin-embedded (FFPE samples). The methods according to the present invention are particularly suited for clinical samples, e.g. FFPE samples.

Generally, the target nucleic acids are ligated to sequences on one or both the 5' and 3' ends. These adaptor sequences comprise sequencing primer sites (i.e., sites to which a sequencing primer will hybridize) to be used in the sequencing methods of the invention.

In some embodiments, the targets subjected to amplification, as discussed below, are of the same or similar length (e.g., a 5-10% variation between targets). In some embodiments, such variation may be kept as small as possible in order to ensure that all templates are uniformly applied.

The amplified products can be immobilized to the support surface (e.g., a glass surface) in a variety of ways. For example, the amplification process may be carried out in solution and the final product is then attached to the support surface. The amplification product may be attached to the solid support at its 5' end or its 3' end. Attachment may be through hybridization to a nucleic acid that is immobilized to the support surface or it may be through interaction of moieties on the end of the amplification product with moieties on the support surface. Examples include the use of biotin or dual biotin labelled DNA (Margulies et al. *Nature* 437:376 (2005)) with streptavidin/avidin/neutravidin coated support surfaces, DIG (digoxigenin) and anti-DIG antibodies or antibody fragments, fluorescein and anti-fluorescein antibodies or antibody fragments (Gore et al. *Nature* 442, 836-9 (2006)), or through the use of heterofunctional cross-linkers such as biotinylated succinimidyl propionate-PEG which can be coupled for example to amine-functionalized glass and used to immobilize biotin-labelled DNA through a streptavidin sandwich (i.e., a nucleic acid biotin streptavidin/avidin/neutravidin-biotin solid support interaction).

The templates may be referred to as being randomly immobilized onto the surface. This means that the templates are not placed on the solid support surface based on sequence. They are however placed on the solid support in a manner that ensures that each template is surrounded by an area (and thus volume) that will not be occupied by another template during the polymerase-mediated incorporation reactions and/or during extension of the template. That is, in some instances, the templates are positioned on the surface at a sufficient distance from each other to prevent any interaction between the templates.

The solid support refers to the element to which the template is bound or immobilized can be comprised of any material, including but not limited to glass or other silica based material, plastic or other polymer based material, provided however that the material is relatively inert to template, primer, polymerase, dNTPs, and other components used in the sequencing reaction and wash. The solid support may or may not be rigid. It may be porous. It may or may not be continuous. In some embodiments, the solid support is a glass slide. In some embodiments, the support is a plurality of beads or particles (such as microparticles) that are themselves immobilized onto a solid support. Such beads may be porous. The support may be a mesh. In some embodiments, the solid support is itself a detector or a sensor such as but not limited to a contact imager.

It is to be understood that a plurality of templates whether identical or different may be tethered to the solid support, provided that each member of the plurality is sufficiently spaced apart from other members so that no overlap occurs between templates.

Typically, the template must be attached to an observable (or detectable) moiety on its free end. This moiety is intended to represent the free end of the template and thus its position and movement in the direction of the force indicates the length of the template. The observable moiety can be any number of moieties and the invention is not limited by its nature. The nature of the observable moiety will dictate the type of sensor or detector suitable to observe (or detect or monitor) changes in the length of the template. In some important embodiments, the observable moiety is a bead such as a microbead, and even more particularly such as a magnetic bead.

The moieties can be attached to the template through a variety of methods and employing a variety of interactions, including but not limited to non-covalent interactions such as biotin/streptavidin, DIG/anti-DIG, and fluorescent/anti-fluorescent binding pairs, as well as covalent interactions, such as those discussed herein in relation to covalent immobilization of templates (or primers) to support surfaces.

The solid support is part of or adjacent to a flow cell. As used herein, a flow cell is a chamber having at least an inlet and an outlet port through which a fluid travels. The solid support to which the template is tethered may be below, above or beside the flow cell, depending on the position of the detection system used to observe the template. The solid support may be a wall of the flow cell including a bottom wall, a side wall, or a top wall.

As will be appreciated, accurate and rapid sequencing of the template is dependent on the extent to which and the rate at which unincorporated nucleotides are removed from the system. Thus, rapid and complete (or near complete) removal of unincorporated nucleotides is important. The microfluidic system must also be designed to maximize washing potentially resulting in smaller wash volumes and wash duration.

Clearance of unincorporated nucleotides can also be facilitated in part or in whole through the use of apyrase which degrades unincorporated dNTPs and renders them unsuitable for further incorporation. The apyrase may be free flowing, added to the wash buffer, and introduced into the flow cell once incorporation of any given nucleotide triphosphate type has ceased (as indicated by the cessation of any above-background movement by the detectable moiety at the end of the template). Alternatively or additionally, apyrase may be fixed or immobilized within the flow cell such as for example to the solid support surface (to which the template is also fixed or immobilized). This may occur through the use of a linker in order to make the enzyme more accessible and to remove any steric hindrance relating to close proximity to the surface. Apyrase may be attached to a variety of linkers that differ in length. In this way, apyrase may be present in a variety of flow streams within the flow cell, including those closer to the walls and those that are closer to or at the center flow streams. As discussed above, it is the flow streams near the walls which travel with low velocity and unincorporated dNTPs present in these flow streams are less likely to be cleared away. Having apyrase in these flow streams should improve removal of these dNTPs. This will increase the likelihood that changes in template length are a result of incorporation of a dNTP newly introduced into the flow cell rather than a residual and unincorporated dNTP that remains in the flow cell after washing.

In some aspects of the invention, the sequencing methods are referred to as sequencing-by-synthesis reactions. This means that determining the sequence of a first nucleic acid requires the synthesis of a second nucleic acid using the first as a template. In this way, the sequence of the second nucleic acid is determined from the order and number of incorporated dNTPs, and the sequence of the first nucleic acid is determined as the complement of the first nucleic acid sequence. The methods of the invention detect dNTP incorporation by a change in length of the template and not by directly observing the addition of the dNTP to nucleic acid being synthesized. As a result, the dNTP can be natural dNTP (i.e., dNTP that lack any modification including any exogenous detectable label such as a fluorophore). As should be clear from this disclosure, the sequencing methods of the invention also require that the template remains intact. Some aspects of the invention involve sequencing methods that are described as occurring in the absence of fluorescence or in a non-fluorescent manner. These characterizations mean that the methods can be carried out without detection of fluorescence, particularly without detection of fluorescence from each incorporated dNTP. Embodiments of these methods therefore may employ natural dNTPs that have not been modified by addition of an exogenous fluorophore. These characterizations do not exclude however the possibility that the observable moiety conjugated to the free end of the template is itself fluorescent. In this latter instance, changes in the length of the template may be visualized via the fluorescence of the observable moiety rather than any fluorescence from individually incorporated dNTP.

Similarly, it will also be understood that the sequencing methods provided herein are able to detect nucleotide incorporation by detecting the observable moiety itself (e.g., as is possible with a CMOS contact imager). Thus, in some embodiments, the observable moieties are detected directly and without the need for an enzyme-mediated event. An example of enzymatically detected nucleotide incorporation is pyrosequencing coupled with sulfurylase and luciferase mediated detection of released inorganic pyrophosphate. (See Leamon and Rothberg, *Chemical Reviews*, "Cramming More Sequencing Reactions onto Microreactor Chips", 2006.) Thus, aspects of the invention are referred to as non-enzymatic methods (or as detecting nucleotide incorporation non-enzymatically) since nucleotide incorporation can be detected in the absence of enzyme-generated signals.

In various embodiments, an analyte of particular interest is hydrogen ions, and large scale ISFET arrays according to the present disclosure are specifically configured to measure pH. In other embodiments, the chemical reactions being monitored may relate to DNA synthesis processes, or other chemical and/or biological processes, and chemFET arrays may be specifically configured to measure pH or one or more other analytes that provide relevant information relating to a particular chemical process of interest. In various aspects, the chemFET arrays are fabricated using conventional CMOS processing technologies, and are particularly configured to facilitate the rapid acquisition of data from the entire array (scanning all of the pixels to obtain corresponding pixel output signals). A preferred sequencing system is the Ion PGM System, however, other sequencing system based on proton detection are also contemplated. For example, pyrosequencing systems and Illumina sequencing-by-synthesis are options. With respect to analyte detection and measurement, it should be appreciated that in various embodiments discussed in greater detail below, one or more analytes measured by a chemFET array according to the present disclosure may include any of a variety of chemical substances that provide relevant information regarding a chemical process or chemical processes of interest (e.g., binding of multiple nucleic acid strands, binding of an antibody to an antigen, etc.). In some aspects, the ability to measure levels or concentrations of one or more analytes, in addition to merely detecting the presence of an analyte, provides valuable information in connection with the chemical process or processes. In other aspects, mere detection of the presence of an analyte or analytes of interest may provide valuable information. The most preferred sequencing method involves the use of Ion Torrent's PGM System, i.e. NGS sequencing methods involving ion semiconductor sequencing.

In another aspect, the invention relates to a method for sequencing nucleic acids comprising fragmenting a template nucleic acid to generate a plurality of fragmented nucleic acids, attaching one strand from each of the plurality of fragmented nucleic acids individually to beads to generate a plurality of beads each having a single stranded fragmented nucleic acid attached thereto, delivering the plurality of beads having a single stranded fragmented nucleic acid attached thereto to a chemFET array having a separate reaction chamber for each sensor in the area, and wherein only one bead is situated in each reaction chamber, and performing a sequencing reaction simultaneously in the plurality of chambers.

The invention contemplates performing a plurality of different sequencing reactions simultaneously within the same flow cell or on the same solid support. Each sequencing reaction yields information about one template immobilized on the solid support. The number of templates that can be sequenced in a single run will depend on the expected length of the template and the area of the solid support. Therefore depending on the embodiment, at least 100, at least 200, at least 300, at least 400, at least 500, at least 600, at least 700, at least 800, at least 900, or at least 1000 templates may be immobilized on a solid support and thus sequenced simultaneously. In still other embodiments, 100-500, 100-750, 100-1000, 500-1000, 600-1000, 700-1000, 800-1000, 900-1000, 1000-2000, 2000-3000, 3000-4000, 4000-5000, 5000-10000, or more templates may be sequenced simultaneously.

The sequencing reaction is carried out by incorporating dNTPs into a newly synthesized nucleic acid strand that is hybridized to the template. The newly synthesized strand may derive from a primer that is bound to the template or from other molecule from which polymerase-mediated extension can proceed.

In one non-limiting example, the sequencing reaction may be commenced by contacting templates with primers under conditions that permit their hybridization, and contacting template/primer hybrids with polymerases. Such contacting may occur before, during and/or after immobilization to the solid support. In an important embodiment, it occurs following immobilization to the solid support.

Once the primers and polymerases are bound to the template, repeated cycles of reagents are flowed into and through the flow cell. When the reagent flow contains a nucleotide that is complementary to the nucleotide on the template that is directly downstream of the 3' end of the primer, the polymerase will incorporate the dNTP. If contiguous downstream positions on the template are occupied by identical nucleotides (referred to herein as a homopolymer), the polymerase will incorporate an identical number of complementary dNTPs. Such incorporation will cease when the dNTP in flow is not complementary to the next available nucleotide on the template. The amount of flowed dNTP and the time of such flow will respectively exceed the number of complementary bases on the template and the time needed to incorporate all possible dNTPs.

Importantly, incorporation of the complementary dNTPs occurs at more than one of the bound primers. More preferably, incorporation occurs at least 10%, at least 25%, at least 50%, at least 60%, at least 70%, at least 80%, at least 90%, or at all of the bound primers. The percentage of primers may depend upon the number of target copies in the template. For some embodiments, incorporation occurs at least 30, at least 35, at least 40, at least 45, at least 50, at least 60, at least 70, at least 80, at least 90, at least 100 or more primers per individual template. It will be understood that the invention contemplates incorporating dNTPs at as many of the hybridized primers on a given template in order to increase signal to noise ratio by increasing the magnitude of the length change that occurs (whether it is an increase or decrease in length).

As part of the sequencing reaction, a dNTP will be ligated to (or "incorporated into" as used herein) the 3' of the newly synthesized strand (or the 3' end of the sequencing primer in the case of the first incorporated dNTP) if its complementary nucleotide is present at that same location on the template nucleic acid. Incorporation of the introduced dNTP converts a single stranded region of the template into a double stranded region, and this conversion is then reflected in a change in length of the template under tension. The change in length is detected by determining and monitoring the position of the observable moiety (e.g., a bead) located at the free end of the template. Therefore, if the bead position is unchanged after any given flow through, then no dNTPs have been incorporated and one can conclude that the flow through dNTP was not complementary to the next available nucleotide in the template. If a change in position of the moiety is detected, then the flow through dNTP was complementary and was incorporated into the newly synthesized strand. dNTPs may be flowed in any order provided the order is known and is preferably kept constant throughout the sequencing run.

A typical sequencing cycle for some aspects of the invention may include washing of the flow chamber (and wells) with wash buffer, measurement of the position of the observable moiety tethered to the end of the template nucleic acid, introduction of a first dNTP species (e.g., dATP) into the flow chamber in the presence of polymerase, measurement of the position of the observable moiety, flow through of apyrase optionally in wash buffer, flow through of wash buffer, introduction of a second dNTP species in the presence of polymerase, and so on. This process is continued until all 4 dNTP (i.e., dATP, dCTP, dGTP and dTTP) have been flowed through the chamber and allowed to incorporate into the newly synthesized strands. This 4-nucleotide cycle may be repeated any number of times including but not limited to 10, 25, 50, 100, 200, 300, 400, 500, 600, 700, 800, 900, 1000 or more times. The number of cycles will be governed by the length of the target being sequenced and the need to replenish reaction reagents, in particular the dNTP stocks and wash buffers. Thus, the length of sequence that may be determined using the methods of the invention may be at least 50 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, up to and including 1000 nucleotides, 1500 nucleotides, 2000 nucleotides or more nucleotides Suitable polymerases can be DNA polymerases, RNA polymerases, or subunits thereof, provided such subunits are capable of synthesizing a new nucleic acid strand based on the template and starting from the hybridized primer. An example of a suitable polymerase subunit is the exo-version of the Klenow fragment of *E. coli* DNA polymerase 1 which lacks 3' to 5' exonuclease activity. Other suitable polymerases include T4 exo-, Thenninator, and Bst polymerases. The polymerase may be free in solution (and may be present in wash and/or dNTP solutions) or it may be fixed to the solid support, one or more walls of the flow cell, the template, or the primers.

It will be understood that the sequencing methods provided herein have a number of applications including without limitation determining partial or complete nucleotide sequence of a nucleic acid (or a collection of nucleic acids such as exist in a genome, including mammalian genomes and more particularly human genomes), determining the presence or absence of a nucleic acid in a sample (as can be useful in for example diagnostic and forensic methods), determining whether the nucleic acid comprises a mutation or variation in sequence (such as for example an allelic variation including a single nucleotide polymorphism), determining whether a known nucleic acid has undergone mutation resulting in the generation of a new species (such as may be the underlying cause of antibiotic resistant microorganisms), determining the presence of a genetically modified organism or genetically engineered nucleic acids, determining whether and what genetic differences exist between two samples (such as for example normal tissue and diseased tissue), determining what therapeutic regimen will be most effective to treat a subject having a particular condition as can be determined by the subject's genetic make-up, and genotyping (e.g., analyzing one or more genetic loci to determine for example carrier status). In some of these embodiments, the nucleotide sequence determined using the methods of the invention may be compared to a known or reference sequence in order to orient the obtained sequence and/or to identify differences between the two. This may help to identify genetic variation and mutation. The known or reference sequence may be a previously determined sequence (for example, resulting from the complete genomic sequencing of a species).

The methods described herein can also be used to aid in the identification and treatment of condition. For example, the methods can be used for identifying a sequence associated with a particular condition or for identifying a sequence that is used to diagnose the absence of a particular condition. The samples being analyzed may be from any subject including humans. The condition may be cancer or an infection.

The methods can also be used to identify a sequence associated with a positive response to an agent. The method may comprise sequencing DNA from a plurality of subjects that exhibited a positive response and from a plurality of subjects that exhibited a negative response to an agent using one or more sequencing methods provided herein, and identifying a common sequence in the plurality of subjects that exhibited a positive response or from the subjects that exhibited a negative response that this sequence is not present in the other plurality of subjects. Preferably, the subject is a mammal, and more preferably a human.

The methods described herein may be automated such that the sequencing reactions are performed via robotics. In addition, the sequencing data obtained from a detector or a sensor may be input to a personal computer, a personal digital assistant, a cellular phone, a video game system, or a television, so that a user can monitor the progress of the sequencing reactions remotely.

The invention further contemplates kits comprising the various reagents necessary to perform the amplification and/or sequencing reactions and instructions of use according to the methods set forth herein.

The methods provided herein are dependent upon detecting single nucleotides at each copy of a target in the template. The limit of resolution is dependent upon the resolution of the detection system used.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

Aspects of the Invention

The present invention provides a new method of detecting the presence of a nucleic acid comprising a target sequence in a sample, comprising Next Generation Sequencing, wherein a system controls, i.e. positive and/or a negative control is/are used, which preferably does not affect the sensitivity of the nucleic acid detection method.

The present invention is based on the use of control nucleic acids, also referred to as Systems Control (SC) that may be added ("spiked") into reaction vessels containing sample material to be analysed in a diagnostic (but also in research) assay. The controls are defined in more detail in the appended claims.

It was surprising to realize that the control nucleic acids of the present invention may be used in NGS-based diagnostic methods and allow determining whether or not the extraction and the subsequent NGS method steps, e.g. amplification of nucleic acid, library preparation and sequencing, fulfil reliable quality standards, and that the NGS workflow is fully functional. At the same time the control nucleic acids of the present invention permit monitoring whether or not a DNA contamination occurred. These controls are ideally suitable as quality controls that are required to meet mandatory regulatory requirements. It was also surprisingly noticed that only very low amounts of the control nucleic acids are required to achieve the objectives set out above. It was noted that such low amounts of control nucleic acids do not negatively influence the extraction, amplification and sequencing reaction (or other steps in NGS) of nucleic acids that are derived from samples to be investigated.

A negative control reaction is typically carried out in a separate reaction vessel, wherein only buffer is added to this specific vial instead of a sample. The presence of the target sequence in the negative control indicates that the samples have been contaminated.

In a first aspect, the invention provides nucleic acid controls for a target nucleic acid sequence-specific Next Generation Sequencing-based diagnostic method, wherein said nucleic acid control comprises at least one nucleic acid control sequence that is different from the target nucleic acid sequence. It is possible, however, that the control comprises more nucleic acid control sequences, which may be found on separate or the same nucleic acid molecule.

The nucleic acid control sequence can be derived from any organism, microorganism or part thereof, e.g. an organ, as long as the control sequence is different from target sequences the organism, microorganism or organ from which the target sequence is derived. For example, when a sample of a human patient is analyzed, the control sequence may be derived from a non-human source to ensure specific identification and at the same time avoid any cross-reactivity of the materials used.

In a further aspect, the nucleic acid control may be selected from a group comprising viral, bacterial, fungal and pathogen-derived nucleic acids, or nucleic acids derived from animal, plant, or nucleic acids that are derived from an organ or body part that is different from the organ or body part that is analysed for the presence or absence of said target nucleic acid sequence.

In one aspect of the invention, the nucleic acid control is selected from viral nucleic acids, e.g. from nucleic acids that are derived from animal or plant viruses. The nucleic acid sequence is generally used in a way that infectious potential is ruled out so that no risk for staff handling the controls or the environment exists.

In a further aspect, the nucleic acid control sequence is selected from nucleic acids that are derived from Tobacco Mosaic Virus (TMV). These sequences may be wild-type sequences, i.e. those found in nature, or the sequences may be modified, i.e. the sequences may contain mutations, additions, deletions, inversions of nucleic acid residues. It is possible that mutant sequences serve as control nucleic acids, e.g. TMV derived nucleic acids that have been so modified that they carry a traceable change when compared with the wild-type sequence. It is possible to mutate TMV by mutation, addition, deletion, or inversions of nucleic acid residues. TMV nucleic acids used as nucleic acid controls are examples for suitable non-human sequences. One advantage of such non-human sequences, e.g. TMV nucleic acids, is that these sequences can serve as negative controls when the target nucleic acid sequences are derived from a human being.

In a further aspect of the invention, the nucleic acid control comprises at least two different nucleic acid control sequences. These sequences may differ in at least one nucleic acid residue, but it is possible also to modify more residues.

In another aspect, the control comprises at least one wild-type nucleic acid sequence and at least one mutant of said wild-type nucleic acid sequence, e.g. wild-type and mutant non-human sequences, such as TMV sequences. One advantage of using a mixture of wild-type and mutant nucleic acid sequences is that such mixtures can serve as reference material for Variant Calling and to provide a defined mutation rate. This greatly increases sensitivity of the methods according to the present invention. Without reference material, the mutation rate calling (in the target nucleic acids, e.g. in oncogenes) would be less reliable.

The modified control sequence may or may not be artificially mutated, i.e. the mutation may occur in nature or not, as long as the modification can be traced by sequencing in an NGS-based method. It is desired that the results of the NGS assay permit deciding that the nucleic acid controls have been spiked into a sample suspected to contain a target nucleic acid, or that the control nucleic acids were used without sample, e.g. serving as negative internal controls in an NGS-based analysis of nucleic acids. In the latter case, the presence of control sequence(s) and the absence of the target sequences as determined in a given NGS-based sequencing reaction is indicative of the absence of contamination with material derived from the sample, or material derived from any other source, e.g. nucleic acids carried over from prior analyses, the environment, etc.

In some aspects of the invention, the nucleic acid control has a single nucleotide mutation, a mutation of more than one nucleotide, an inversion, deletion or addition of nucleic acid residues.

In a still further aspect of the invention, a mixture of control nucleic acids is provided. The mixture can be used in a target nucleic acid sequence-specific Next Generation Sequencing-based diagnostic method and comprises at least two nucleic acid controls at a predetermined ratio. For example, if an NGS-based diagnostic method or assay aims at detecting variants at a certain variant frequency level (e.g. 25%, 20%, 15%, 10%, 5%, 4%, 3%, 2%, 1%, or below 1%) different control sequences are mixed to reflect such variant frequency level. For example, when a variant frequency level of 5% should be detected, one control nucleic acid (for example TMV wild-type) is mixed with 5% of another control nucleic acid (for example TMV carrying one modification, e.g. a single point mutation, a triplet mutation, an inversion, deletion, or the like). The resulting mixture of 95% wild-type control nucleic acid sequence and 5% mutant control nucleic acid can be used to verify that the NGS-based method is capable of correctly detecting the variant frequency level. The person skilled in the art knows how to determine accurately the quantity of variant nucleic acids, i.e. the amount of variant (or mutant/modified) nucleic acids that should be mixed with the wild-type nucleic acids serving as controls in the methods of the present inventions or in inventive mixtures.

Also provided are kits suitable for the detection of target nucleic acids in sequence-specific Next Generation Sequencing-based diagnostic methods. These kits comprise at least one of the nucleic acid controls as defined above, or a nucleic acid control mixture as detailed above. Further, optionally the kits may comprise additional reagents for Next Generation Sequencing-based diagnostic methods, e.g. chemical reagents, instruction leaflets, and the like.

Also provided herein are Next Generation Sequencing-based diagnostic methods, comprising extracting nucleic acid material from a sample and a control sample. The control sample is prepared prior to extraction. These methods further comprise subjecting the extracted nucleic acid material to a Next Generation Sequencing method, e.g. ion semiconductor sequencing. In some aspects, the Next Generation Sequencing-based diagnostic methods provided herein, comprise a control sample which contains sample material supplemented with any of the above mentioned nucleic acid controls or nucleic acid control mixtures.

In further aspects of the invention, the Next Generation Sequencing-based diagnostic method aims at the detection of the presence or absence of target sequences derived from an infectious agent or from an oncogene. It is possible, or course, to analyze more than one targets in one NGS run. Further, the NGS methods may use samples obtained from one or more sources, e.g. one human patient or many human patients. It is possible also to use sample material from one source and target different nucleic acid sequences. At least one NGS-analysis is conducted with a sample from one source, that serves as control sample, i.e. the sample was spiked with at least one of the above nucleic acid controls or a mixtures of the present invention. When samples from more than one source are used, or if the a sample from one source is analyzed with respect to different targets, for each source there may be a control, or for each target there may be a control.

Accordingly, the Next Generation Sequencing-based diagnostic methods according to the invention allow for the detection and analysis of the presence or absence of a target sequence derived from an infectious agent or from an oncogene. The presence of nucleic acid control sequence subsequent to the sequencing reaction are indicative of a successfully accomplished nucleic acid extraction from the samples.

As pointed out above, the Next Generation Sequencing-based diagnostic methods of the present invention may further comprise a contamination control, i.e. a negative control. To this end a control nucleic acid that was not added to sample material is subjected to the NGS workflow. The contamination control comprises at least one nucleic acid control as defined above or a nucleic acid control mixture as defined above. The Next Generation Sequencing-based diagnostic method comprises subjecting the contamination control to a target nucleic acid specific sequencing reaction, wherein the absence of detection of a target nucleic acid specific sequence in the contamination control and the detection of the presence of a control nucleic acid specific sequence are indicative of the absence of contamination.

In some embodiments of the invention, said sample is a clinical sample, wherein said clinical sample is preferably from a human subject. It can be preferred that said clinical sample is a tissue sample or a body fluid sample. Said sample may e.g. be a tissue sample gained from the respiratory tract, the gastrointestinal tract or from a transplant after transplantation. Further, said sample may in particular be a body fluid sample selected from the group consisting of blood, plasma, serum, lymphatic fluid and saliva.

In another preferred embodiment, the target nucleic acid may be a nucleic acid from a microorganism. Preferably, said microorganism is selected from the group consisting of bacteria, archaea, protozoa, fungi and viruses. In a particularly preferred embodiment, said microorganism is a bacterium selected from the group consisting of Group A *Streptococcus*, *Mycobacterium tuberculosis* Complex members including *Mycobacterium tuberculosis*, *Mycobacterium africanum*, *Mycobacterium bovis*, *Mycobacterium canetti* and *Mycobacterium microti*, *Salmonella enterica* spp., *Clostridium difficile*, Vancomycin-resistant *enterococcus* and Methicillin-resistant *Staphylococcus aureus*. In another particularly preferred embodiment, said microorganism is a virus selected from the group consisting of adenovirus, influenza virus, avian influenza A (H7N9) virus, Middle East Respiratory Syndrome Coronavirus, norovirus, BK virus, cytomegalovirus, Epstein-Barr virus, herpes simplex virus 1, herpes simplex virus 2, Varicella-Zoster virus, enterovirus, HIV-1, hepatitis B virus, hepatitis C virus, Dengue virus and Chikungunya virus.

In some embodiments, the target nucleic acid may be an oncogene, preferably a human oncogene, e.g. an oncogene selected from the group consisting of BCR-ABL major, BCR-ABL minor, BCR-AML1 ETO, PML-RARA, BRAF V600 mutants, KRAS mutants, NRAS mutants, EGFR, KIT, or PIK3CA. In embodiments of the invention, the methods of the present invention may thus be used to detect the presence of one or more oncogenes in a sample.

The control nucleic acids of the present invention may be used in NGS-based diagnostic methods in amounts that allow for the specific detection and/or expected detection level. The presence of controls in sample reactions should not negatively influence the outcome of the results. That means, there should not be interference of the control nucleic acids with the extraction, amplification and sequencing, or any other NGS method steps, in terms of sufficient quality and/or sufficient quantity of the target nucleic acids, which could lead to false interpretations of the results.

Depending on the sensitivitiy required for a specific target sequence in terms of variant frequency (vf), the quantity of the controls of the present invention is chosen. For example, when it is desired to detect 5% variant frequency (vf), 5 fg of the systems control of the invention (constructed with 5% variant frequency) may be used to provide more than 1000 fold coverage of the target. If the desired sensitivity changes to 1% vf, it is possible to use 20 fg of the controls of the invention (constructed with 1% variant frequency) to provide a 10,000 fold coverage of the target sequence. It may be sufficient that 0.1 to 1000 fg, preferably 0.1 to 100 fg, more preferably 1.0 to 50.0 fg, 1.0 to 25 fg, more preferably 1.0 to 10.0 fg, e.g. 5 fg of control nucleic are present in a NGS reaction. For example, one may add about 100 fg to 1000 fg to the samples. However, depending on the source of the target material the correct amount may be adapted. To this end, reference material from different sources, or material that has been physically treated to resemble the desired source material, may be subjected to a titration analysis of the amounts of control nucleic acid to determine the suitable amount required in each specific assay. For example, the extraction of nucleic acids from plant material or animal tissues may require different pretreatments. Depending on the expected yield or loss of nucleic acids from different sources, the quantitative input of control material may be different.

FIGURES

FIG. 1 provides an overview on an inventive NGS method according to the invention. A, Eight reactions are conducted in this schematic representation. In the first reaction well (1), only a positive systems control (SC) is added, i.e. this reaction does not contain any sample material. The reaction wells (2 to 8) contains FFPE sample material and spiked-in SC. Also shown are devices used in the automated workflow. In B and C, the results of the sequencing reaction are shown. While the positive control and spike-in control SC sequences in wells (1) and (2 through 8) were detected as desired, target sequences were not present in well (1). On the other hand, the sequencing reaction of oncogenes present in the FFPE samples in wells (2) to (8) was successfully accomplished. The systems control used in well (1) was a mixture of plasmids comprising wild-type non-human nucleic acid sequences and plasmids comprising mutations in said non-human nucleic acid sequence. The plasmids were mixed so that the mutations were present at 5% variant frequency, and the remainder was made up of plasmid comprising wild-type non-human nucleic acid sequences. As FFPE reference material, cells lines obtained from Horizon Discovery Ltd., UK. These cell lines were engineered to carry known mutations present at defined variant frequencies (2-33%).

Figure 2:
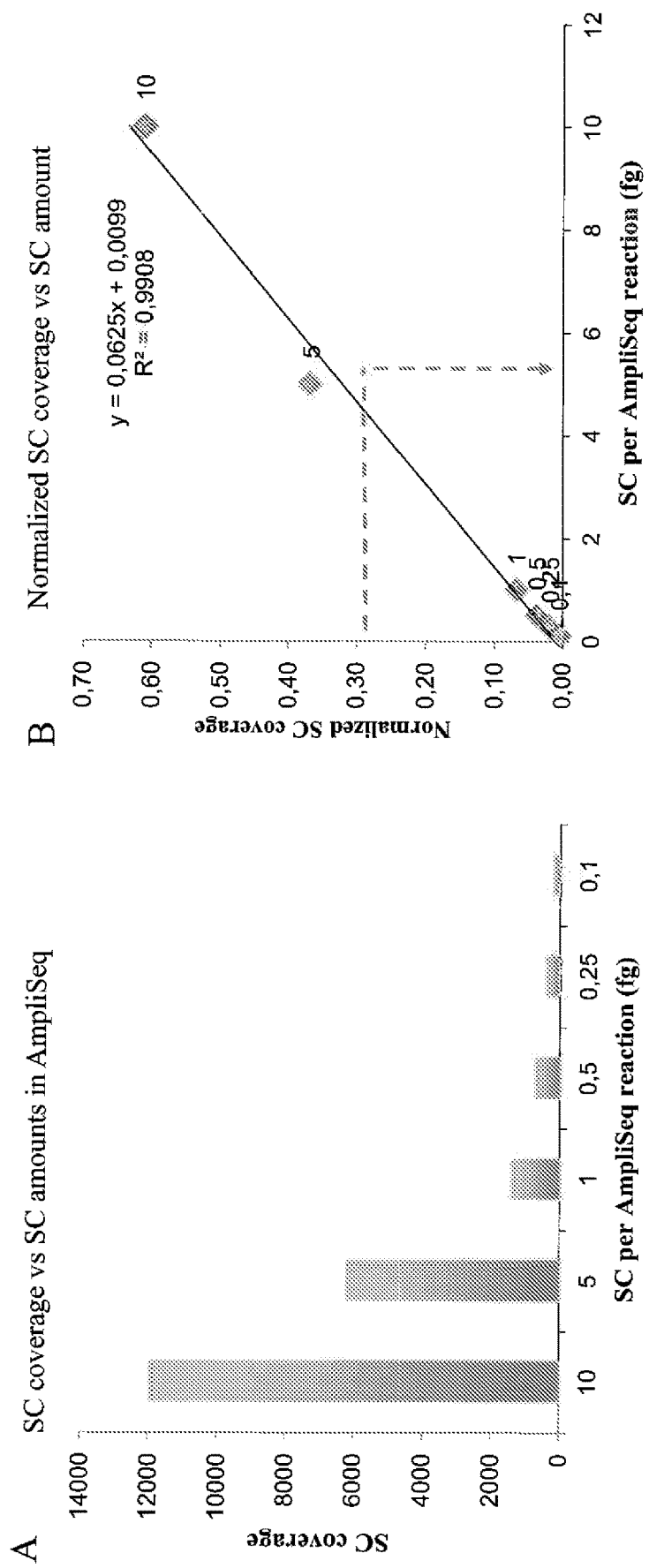

FIG. 2 shows the results of bar-coded NGS runs comprising FFPE-DNA with 10, 5, 1, 0.5, 0.25, and 0.1 fg SC added in each PCR (AmpliSeq) reaction, together with a similar DNA sample with 100 fg SC spiked into the sample at the beginning of the automated workflow. A, bar-chart of SC coverage vs. known amounts of SC added (manually) to each sequencing reaction before AmpliSeq (Life technologies). The FFPE DNA used for this part of the testing must not be spiked with SC at the onset of the workflow. The resultant SC coverage was proportional to the levels of SC added into each AmpliSeq reaction. B, Plot of SC coverage vs SC levels showed a linear relationship between SC coverage and SC level. Here, the SC coverage was normalized with mean coverage of all amplicons in the sample. By interpolation (red dotted line), the FFPE sample with 100 fg of SC spiked at the beginning of the extraction steps will produce an SC coverage comparable to that from a sample with 5 fg of SC added in the AmpliSeq reaction. This testing demonstrated that SC can be recovered after the automated workflow, and its level in the sequencing reaction can be estimated. Hence, SC can be used as a spike-in control. (Note that all the samples used for this sequencing run had matched DNA inputs, except for the SC).

Figure 3:
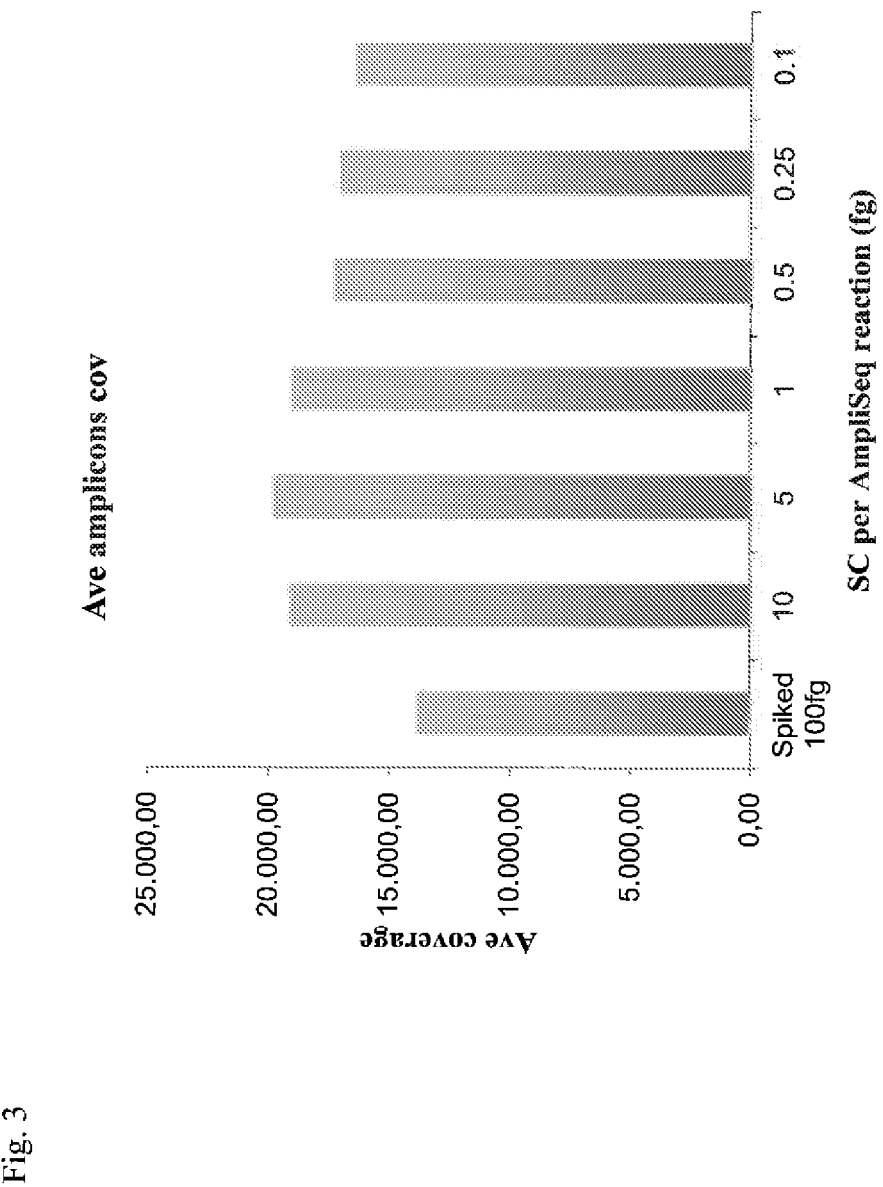

FIG. 3 shows the same barcoded runs as described in FIG. 2 above. The bar-chart shown here is a plot of the mean coverage of target amplicons vs. varying levels of SC added in each sample. Here, increasing SC from 0.1 through 10 fg does not suppress the mean coverage in the samples, showing that at these levels (0.1 to 10 fg) SC does not adversely affect the amplification of the target amplicons.

Figure 4:
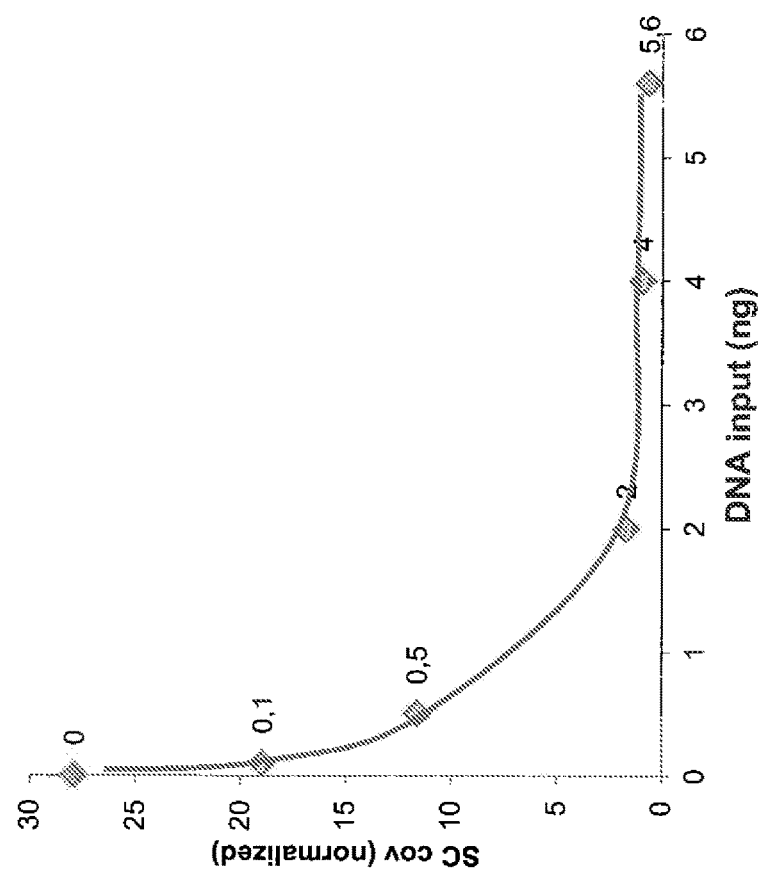
Figure 4:
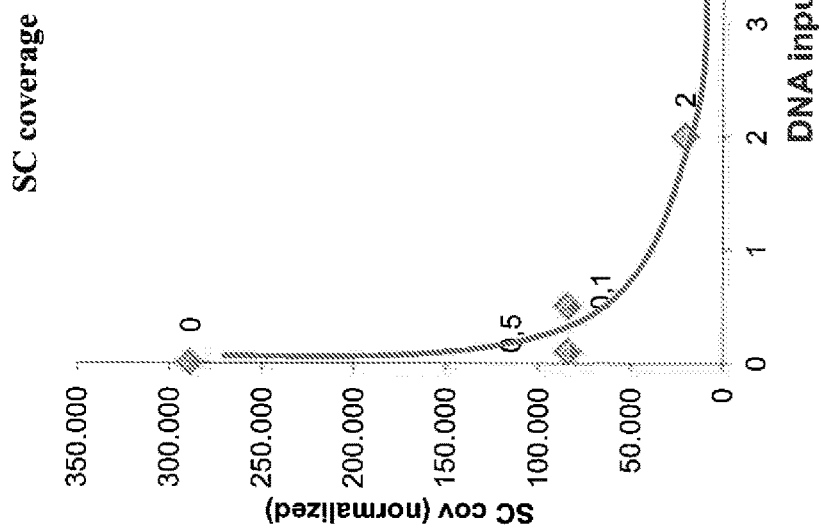

FIG. 4 shows an experiment with fixed SC (5 fg added in each AmpliSeq reaction) with varied DNA inputs (0.1-5 ng). Here, SC coverage was inversely proportional to average targets coverage. Non-normalized and normalized SC coverage were plotted against DNA inputs (A and B, respectively). The data show that the SC levels vary according to DNA input in a sample, and hence may be useful as a checkpoint for low DNA inputs.

Figure 5:
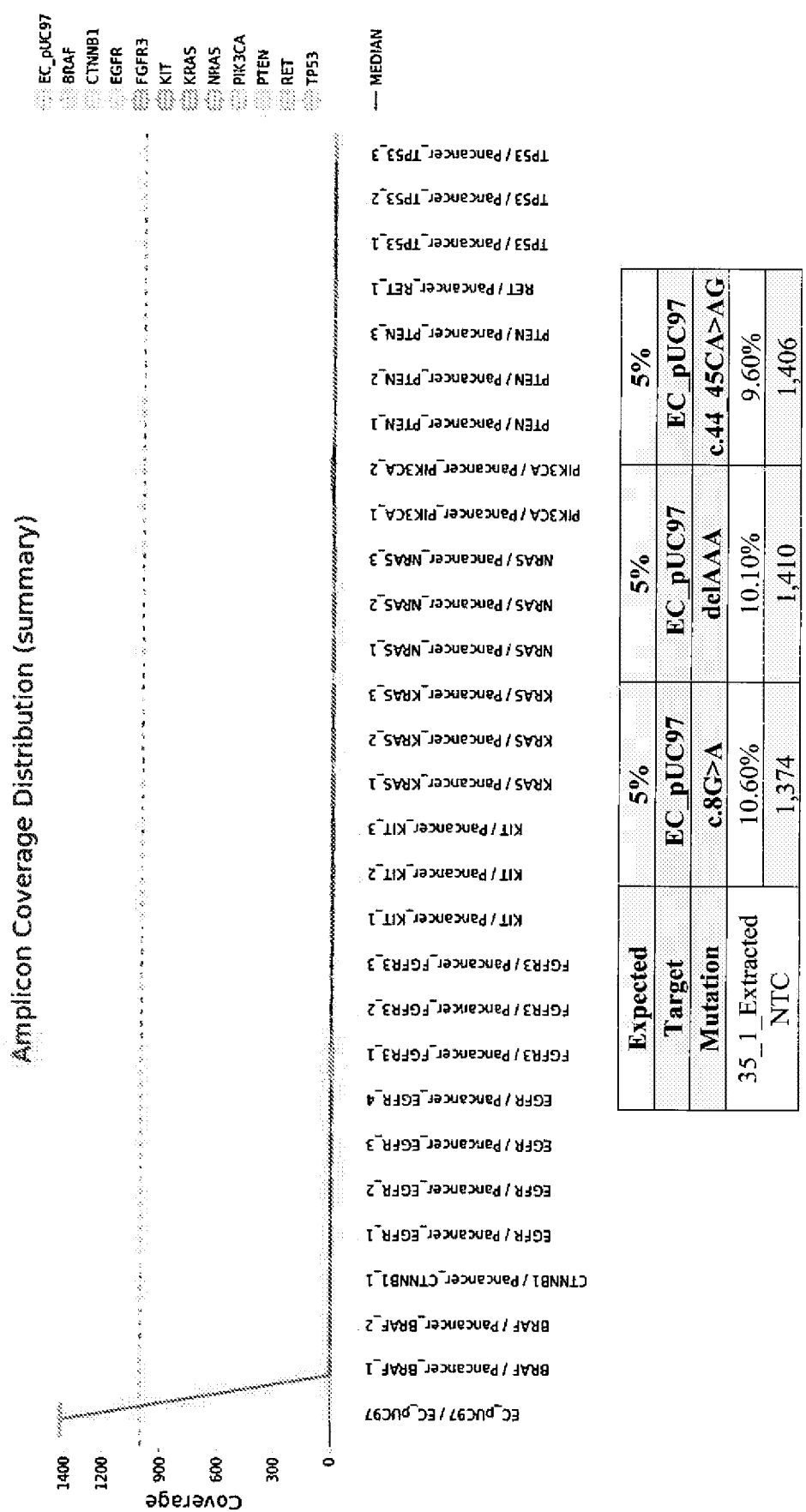

FIG. 5 shows the negative control well (well #1) containing only the SC. This data demonstrate the usefulness of the SC as a positive control and negative control (NTC). A. Sequences for the SC were detected but those for human target sequences were not. B, All three mutations in SC were recovered after Next Generation Sequencing. The amplicon for the SC is denoted as EC_pUC97.

FIG. 6 comprises Table 1 that shows the logic table involved in the use of Systems Control (SC) as a quality (QC) concept for NGS. A successful sequencing run requires the recovery of sequences for the spike-in SC in each sample, and those for the SC in well (1) (stand alone SC). In addition, there should be no sequences mapping to human targets in well (1). In this way, well (1) acts as both an external, overall positive control for the run, as well as the non-template control (NTC). The spike-in SC acts as the extraction and in-sample positive control for each sample. For a successful sample, the expected target amplicons are expected to be successfully detected. The failure to recover the SC in well (1) indicates a major failure of the workflow and the run would be considered invalid. Target amplicons, even if successfully sequenced, may not be reliable. For a sample that failed to generate target amplicons but pass the criteria for the stand alone SC in well (1), the presence of spike-in SC indicates workflow is operating, but the sample has insufficient amplifiable DNA. Absence of the spike-in indicates presence of inhibitors in the sample.

It is to be understood that while the invention has been described in conjunction with the embodiments described herein, that the foregoing description as well as the examples that follow are intended to illustrate and not limit the scope of the invention. Other aspects, advantages and modifications within the scope of the invention will be apparent to those skilled in the art to which the invention pertains. All patents and publications mentioned herein are incorporated by reference in their entireties.

The following examples are put forth so as to provide those of ordinary skill in the art with a complete disclosure and description of how to make and use the compositions of the invention. The examples are intended as non-limiting examples of the invention. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

The invention claimed is:

1. A Next Generation Sequencing-based diagnostic method comprising:
   extracting nucleic acid material from a test sample,
   extracting nucleic acid material from at least one control sample, wherein the at least one control sample is prepared prior to extraction,
   subjecting the extracted nucleic acid materials to a Next Generation Sequencing method,
   wherein the at least one control sample comprises a first nucleic acid control, wherein said first nucleic acid control comprises at least one wild-type nucleic acid control sequence that is different from a target nucleic acid sequence and additionally comprises a second nucleic acid control sequence, wherein the second nucleic acid control sequence is a mutant of said wild-type nucleic acid sequence,
   and wherein the second nucleic acid control sequence is present at a predetermined ratio in comparison to the first nucleic acid control sequence.

2. The Next Generation Sequencing-based diagnostic method according to claim 1, wherein the target nucleic acid is derived from an infectious agent or from an oncogene.

3. The Next Generation Sequencing-based diagnostic method according to claim 1, further comprising extracting nucleic acid material from a contamination control in addition to the extracting nucleic acid materials from the test sample and the at least one control sample.

4. The Next Generation Sequencing-based diagnostic method according to claim 3, wherein the contamination control comprises at least one nucleic acid control sequence that is different from the target nucleic acid sequence wherein the contamination control does not comprise test sample material.

5. The Next Generation Sequencing-based diagnostic method according to claim 3, comprising subjecting the contamination control to a target nucleic acid-specific sequencing reaction.

6. The Next Generation Sequencing-based diagnostic method according to claim 4, comprising subjecting the contamination control to a target nucleic acid specific sequencing reaction, wherein the absence of detection of a target nucleic acid-specific sequence in the contamination control and the detection of the presence of a control nucleic acid-specific sequence are indicative of the absence of contamination.

7. The Next Generation Sequencing-based diagnostic method according to claim 5, wherein the test sample is a clinical sample derived from a human subject, and wherein the at least one nucleic acid control sequence is provided as a component of a plasmid comprising wild-type and/or mutant sequence of a non-human virus, and further wherein the non-human virus is selected from animal viruses not infecting humans, and plant viruses, or wherein the at least one nucleic acid control sequence has been artificially designed and has no equivalent in nature.

8. The Next Generation Sequencing-based diagnostic method according to claim 5, wherein the first nucleic acid control comprises a non-human nucleic acid sequence or a viral nucleic acid sequence.

9. The Next Generation Sequencing-based diagnostic method according to claim 1, wherein the at least one control sample is present in an amount of 0.1 to 10 fg subsequent to extraction of the nucleic acid material from the sample and the at least one control sample.

10. The Next Generation Sequencing-based diagnostic method according to claim 9, wherein the target nucleic acid is derived from an infectious agent or from an oncogene.

11. The Next Generation Sequencing-based diagnostic method according to claim 1, wherein the test sample is a clinical sample derived from a human subject, and wherein the first nucleic acid control is a plasmid comprising wild-type and/or mutant sequence of a non-human virus, and further wherein the non-human virus is selected from animal viruses not infecting humans, and plant viruses, or wherein the first nucleic acid control has been artificially designed and has no equivalent in nature.

12. The Next Generation Sequencing-based diagnostic method according to claim 9, further comprising extracting nucleic acid material from a contamination control in addition to the extracting nucleic acid material from the test sample and the at least one control sample, and wherein the contamination control comprises at least one nucleic acid control sequence that is different from the target nucleic acid sequence wherein the contamination control does not comprise test sample material.

13. The Next Generation Sequencing-based diagnostic method according to claim 1, wherein the first nucleic acid control comprises a non-human nucleic acid sequence or a viral nucleic acid sequence.

14. The Next Generation Sequencing-based diagnostic method according to claim 1, wherein the first nucleic acid control comprises a Tobacco Mosaic Virus nucleic acid sequence; or wherein the at least one wild-type nucleic acid control sequence is a Tobacco Mosaic Virus nucleic acid sequence; or wherein the second nucleic acid control sequence is a Tobacco Mosaic Virus nucleic acid sequence.

\* \* \* \* \*